US010172987B2

(12) United States Patent
Bonde

(10) Patent No.: US 10,172,987 B2
(45) Date of Patent: Jan. 8, 2019

(54) SYSTEM AND METHOD FOR HEART PUMP INTERROGATION AND INSPECTION

(71) Applicant: Yale University, New Haven, CT (US)

(72) Inventor: Pramod Bonde, Woodbridge, CT (US)

(73) Assignee: YALE UNIVERSITY, New Haven, CT (US)

( * ) Notice: Subject to any disclaimer, the term of this patent is extended or adjusted under 35 U.S.C. 154(b) by 76 days.

(21) Appl. No.: 14/276,346

(22) Filed: May 13, 2014

(65) Prior Publication Data
US 2014/0336444 A1 Nov. 13, 2014

Related U.S. Application Data

(60) Provisional application No. 61/822,675, filed on May 13, 2013.

(51) Int. Cl.
*A61M 1/10* (2006.01)
*A61M 25/10* (2013.01)
*A61M 1/12* (2006.01)

(52) U.S. Cl.
CPC .......... *A61M 1/1086* (2013.01); *A61M 25/10* (2013.01); *A61M 1/101* (2013.01); *A61M 1/1008* (2014.02); *A61M 1/1018* (2014.02); *A61M 1/122* (2014.02); *A61M 2025/1052* (2013.01); *A61M 2025/1061* (2013.01); *A61M 2205/702* (2013.01)

(58) Field of Classification Search
None
See application file for complete search history.

(56) References Cited

U.S. PATENT DOCUMENTS

| | | | |
|---|---|---|---|
| 5,222,980 A * | 6/1993 | Gealow | A61M 1/1037 417/474 |
| 5,411,016 A | 5/1995 | Kume et al. | |
| 6,059,757 A * | 5/2000 | Macoviak | A61M 25/0075 604/247 |
| 8,197,198 B2 | 5/2012 | Bhunia | |
| 2007/0112325 A1* | 5/2007 | Wieselthaler | A61M 1/10 604/500 |
| 2012/0004564 A1* | 1/2012 | Dobak, III | A61B 5/021 600/510 |
| 2013/0042892 A1* | 2/2013 | Lynch | A61M 1/101 134/22.1 |

(Continued)

OTHER PUBLICATIONS

Slaughter et al., "Clinical management of continuous-flow left ventricular assist devices in advanced heart failure." The Journal of Heart and Lung Transplantation, Apr. 2010, vol. 29, No. 4S, S1-39.

*Primary Examiner* — Erica S Lee
(74) *Attorney, Agent, or Firm* — Riverside Law LLP

(57) ABSTRACT

The present invention relates to systems and methods for in situ inspection, interrogation, and maintenance of heart pump function in subjects with an implanted heart pump. In certain embodiments, the system comprises a catheter assembly deliverable to the inflow port and outflow port of the implanted heart pump. The system comprises additional components used to examine pump function and prevent malfunction. In certain embodiments, the invention allows for temporary, mid-term, or permanent exclusion of the implanted heart pump from cardiac function without surgically removing the pump.

11 Claims, 15 Drawing Sheets

(56) References Cited

U.S. PATENT DOCUMENTS

| | | | |
|---|---|---|---|
| 2013/0274720 A1* | 10/2013 | Brannon | A61B 17/32053 606/1 |
| 2013/0281761 A1* | 10/2013 | Kapur | A61M 1/3659 600/17 |
| 2015/0087890 A1* | 3/2015 | Spanier | A61B 5/6852 600/16 |

* cited by examiner

SYSTEM AND METHOD FOR HEART PUMP INTERROGATION AND INSPECTION

CROSS-REFERENCE TO RELATED APPLICATIONS

This application claims priority to U.S. Provisional Application No. 61/822,675 filed on May 13, 2013, the contents of which are incorporated by reference herein in its entirety.

BACKGROUND OF THE INVENTION

Implantation of a heart pump is often necessary to provide adequate blood supply to the body in subjects with diminished native heart function. However, current pumps are often lacking in their ability to be non-invasively monitored or manipulated in situ. For example, current devices do not allow for the direct measurement of flow. Rather, flow is estimated based on the power consumption that is used by the pump. Further, current continuous flow devices do not have any means for the direct inspection and maintenance that can diagnose dysfunction of the device or prevent or remove harmful clot formation. Clot formation within an implanted heart pump is a serious complication that can hamper pump function, and in some instances require emergency invasive surgery to quickly remove and replace the pump.

In most cases, implantation of a heart pump prevents any reliable method of assessing the function of the native heart tissue. For example, recovery of the native heart cannot be assessed by turning off the pump temporarily in safe fashion. Temporary, mid-term, and permanent in situ exclusion of heart pumps are lacking. This means that if native heart function is determined to have been adequately recovered, the subject requires major surgery for the removal of the device. Further, if the native heart starts to fail again, a new pump would have to be implanted.

Thus, there is a need in the art for systems and method to monitor and maintain heart pump function in situ. The present invention satisfies this unmet need.

SUMMARY OF THE INVENTION

The present invention provides a system for the in situ inspection of an implanted heart pump. The system comprises a catheter assembly including at least one catheter suitable to be delivered into at least one of the inflow port and outflow port of a heart pump implanted in a subject. In one embodiment the catheter assembly comprises a first catheter suitable to be delivered to the inflow port of the heart pump and a second catheter suitable to be delivered to the outflow port of the heart pump.

In one embodiment, at least one of the first and second catheters each comprise an inflatable balloon positioned near the distal end of the catheter, wherein inflation of the balloon occludes fluid flow. In one embodiment, at least one of the first and second catheters each comprise an inner lumen through which one or more additional components is deliverable to an interior chamber of the heart pump. In one embodiment, the one or more additional components include scopes, fluid delivery devices, probes, and brushes.

In one embodiment, the additional component is a scope, and wherein the scope comprises a hollow working channel through which one or more additional components is deliverable to the heart pump. In one embodiment, the one or more additional components include scopes, fluid delivery devices, probes, and brushes.

In one embodiment, the additional component is a fluid delivery device that delivers a solution to the heart pump which reduces blood clot formation in the heart pump. In one embodiment, the solution comprises an anticoagulant, such as heparin, tissue plasminogen activator (tPa), streptokinase, collagenase, proteases, proteolytic agents, superhydrophobic agents, and analogs thereof.

In one embodiment, the system comprises at least two closure devices, wherein the closure devices are suitable to be delivered into the inflow port and outflow port of the heart pump by the catheter assembly, wherein the closure devices occlude blood flow into and out of the heart pump, thereby excluding the heart pump from the blood flow circuit of the subject.

The present invention provides a method for in situ inspection of an implanted heart pump. The method comprises guiding a catheter into the inflow port or outflow port of a heart pump implanted in a subject.

In one embodiment, the method comprises delivering a scope through an inner lumen of the catheter into an interior chamber of the heart pump to allow for visual inspection of the interior of the heart pump.

In one embodiment, the method comprises inflating a balloon positioned at the distal end of the catheter, thereby occluding blood flow.

The present invention provides a method for reducing the presence of blood clots within an implanted heart pump. The method comprises guiding a first catheter to the inflow port of a heart pump implanted in a subject; guiding a fluid delivery device through an inner lumen of the first catheter into an interior chamber of the heart pump; and administering a fluid to the interior of the heart pump, wherein the fluid reduces the presence of blood clots within the heart pump.

In one embodiment, the fluid delivery device is guided to the heart pump via the working channel of a scope, wherein the scope is guided to the heart pump via the inner lumen of the first catheter.

In one embodiment, the fluid comprises an anticoagulant such as heparin, tissue plasminogen activator (tPa), streptokinase, collagenase, proteases, proteolytic agents, superhydrophobic agents, and analogs thereof.

The present invention provides a method for excluding a heart pump from the blood flow circuit of a subject having an implanted heart pump. The method comprises guiding a first catheter to the inflow port of the heart pump; guiding a second catheter to the outflow port of the heart pump; occluding flow into the heart pump by positioning a first occlusion structure at the inflow port; and occluding flow out of the heart pump by positioning a second occlusion structure at the outflow port.

In one embodiment, the first and second occlusion structures each comprise an inflated balloon. In one embodiment, the method comprises assessing the cardiac function of native heart tissue while the heart pump is excluded from the blood flow circuit. In one embodiment, the first and second occlusion structures each comprise a closure device guided to the inflow port and outflow port via the first and second catheter. In one embodiment, the closure device is manufactured from titanium, stainless steel, nitinol, polyethylene terephthalate, polyether ether ketone, polyurethane, or graphene.

The present invention provides a method of measuring the flow rate output of an implanted heart pump. The method comprises positioning a first catheter in the vicinity of the heart pump; delivering a fluid to a first site in the blood stream; measuring a characteristic of the fluid at a second site downstream of the first site; and calculating the flow rate based on the measured change in the characteristic. In one embodiment, the characteristic is temperature.

In one embodiment, the first site is at the inflow port of the heart pump, and the second site is at the outflow port of the heart pump, wherein the fluid is delivered to the first site via a fluid delivery device guided into the inflow port of the heart pump via the inner lumen of a first catheter.

In one embodiment, the first site is at the outflow port of the heart pump, and the second site is downstream of the outflow port of the heart pump, wherein the fluid is delivered to the first site via a fluid delivery device guided into the outflow port of the heart pump via the inner lumen of a first catheter.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1A and FIG. 1B, are a set of images depicting the implantation and function of two exemplary types of heart pumps, an axial pump (FIG. 1A) and centrifugal pump (FIG. 1B).

FIG. 2A and FIG. 2B, are a set of images depicting the distal region of an exemplary catheter of the present invention, comprising an inflatable region comprising an inflatable balloon. FIG. 2A depicts the catheter prior to inflation of the balloon, while FIG. 2B depicts the catheter after inflation.

FIG. 8A and FIG. 8B, depicts the delivery of a catheter and inflation of a balloon positioned at the distal end of the catheter to the inflow and outflow ports of an axial pump (FIG. 8A) and centrifugal pump (FIG. 8B). Delivery of the catheters and inflation of the balloons allows for temporary occlusion of blood flow through the pump and subsequent inspection or maintenance of pump function.

FIG. 9A and FIG. 9B, depicts the delivery of a fluid delivery device through the catheter and into the inflow ports of an axial pump (FIG. 9A) and centrifugal pump (FIG. 9B). The delivered fluid washes out the pump FIG. 10, comprising

FIG. 11A and FIG. 11B, depicts the placement of closure devices at the inflow port and outflow port of an axial pump (FIG. 11A) and centrifugal pump (FIG. 11B), providing mid-term to permanent exclusion of the heart pump from blood flow.

DETAILED DESCRIPTION

Figure 1:
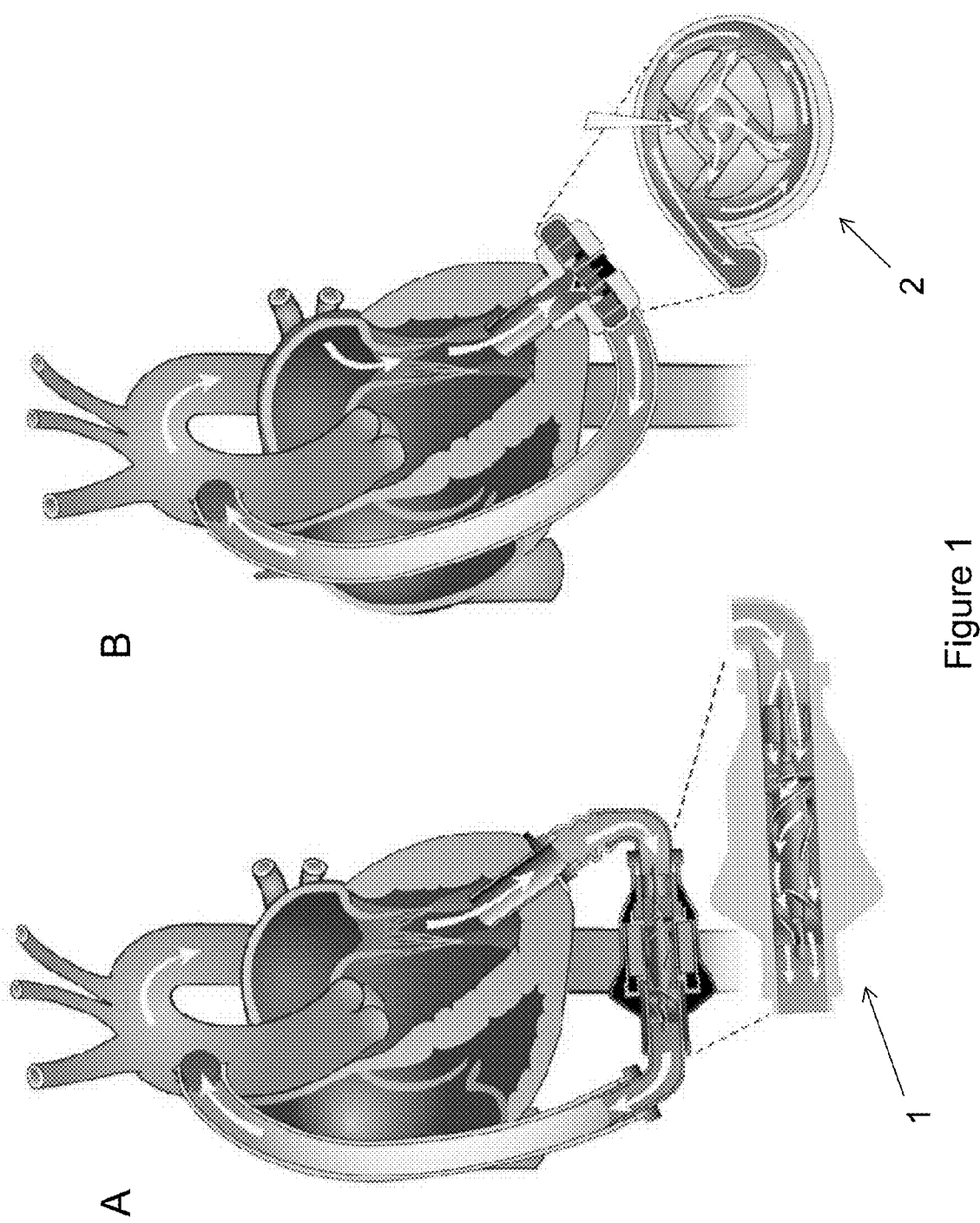
FIG. 1, comprising

The present invention relates to systems and methods for in situ inspection, interrogation, and maintenance of heart pump function. In certain embodiments, the system comprises one or more catheter assemblies deliverable to the inflow port and outflow port of the implanted heart pump. The system comprises additional components used to visualize the pump components, examine pump function and prevent malfunction. In certain embodiments, the invention allows for temporary, mid-term, or permanent exclusion of the implanted heart pump from cardiac function without surgically removing the pump.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, or ±5%, or ±1%, or ±0.1% from the specified value, as such variations are appropriate.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention provides devices, methods, and systems for the in situ interrogation, inspection, and manipulation of the function of an implanted medical device. For example, in certain embodiments, the present invention is used for interrogation, inspection, maintenance and manipulation of heart pump function in a subject in which the heart pump is implanted. The present invention allows for the subject to have routine and minimally-invasive examination, maintenance, or repair performed on their implanted heart pump. Such procedures can safely and easily detect and repair potential malfunctions before they result in catastrophic failures that would require major emergency surgery to replace the heart pump.

In one aspect, the present invention allows for the in situ interrogation, inspection, and manipulation of any heart pump known in the art. For example, the invention may be used in patients having any type of heart pump, including, but not limited to axial pumps, centrifugal pumps, magnetically levitated pumps, ventricular assist devices (VADs), RVADs, LVADs, BiVADs, total artificial hearts, and the like. Commercially available pumps, include, but are not limited to, Novacor, HeartMate® XVE, HeartMate® II, Heartmate® III, INCOR®, EXCOR® Pediatric, Jarvik 2000®, MicroMed DeBakey VAD®, VentrAssist™, MiTiHeart® LVAD, C-Pulse®, HeartWare® VAD (HVAD®), HeartWare MVAD, Circulite®, DuraHeart™ LVAS, Thoratec PVAD™, and Thoratec IVAD™. For example, FIG. 1 depicts two different types of heart pumps, 1 and 2, on which the system and methods of the present invention may be used. Heart pump 1 (FIG. 1A) is an axial pump (e.g. HeartMate® II LVAD), while heart pump 2 (FIG. 1B) is a centrifugal pump (e.g. HVAD® (HeartWare)). The system of the invention allows for catheters and other components to access the inflow port and outflow port of the heart pump in situ for inspection, maintenance, or manipulation of pump function.

The present invention is described herein in relation to the examination and/or maintenance of an implanted heart pump. However, the device, system, and method of the invention are not limited to a heart pump. Rather, the present invention may be used for the examination and maintenance of any implanted medical device, including but not limited to an arteriovenous fistula (native or surgically created), temporary or permanently indwelling catheters, stents within hollow viscus cavity, vascular grafts, implantable drug delivery pumps, and implantable chemotherapy delivery pumps.

In one embodiment, the system of the invention comprises a catheter assembly comprising one or more catheters that may be guided into the inflow port and/or the outflow port of the heart pump. In one embodiment, the system comprises a plurality of catheters, wherein at least one first catheter may be guided into the inflow port of the heart pump and at least one second catheter may be guided into the outflow port of the heart pump.

As used herein, "catheter" refers to a hollow conduit comprising an external sheath and inner lumen. In certain embodiments, one or more devices are guided through the inner lumen of the catheter in order to access at least one internal chamber of the implanted heart pump.

In certain embodiments, one or more catheters are steerable catheters comprising a steering handle and a bendable tip. However, the present system is not limited to any particular type of catheter. Rather, any catheter known in the art that can be guided to the heart and heart pump may be included in the system of the invention. For example, in certain embodiments catheters may be guided to the heart and heart pump by way of an inserted guide wire, using typical procedures known in the art. The catheter may be of any suitable size known in the art. For example, in certain embodiments, the catheter has an external diameter of about 2 to about 20 french. In another embodiment, the catheter has an external diameter of about 4 to about 8 french.

In certain embodiments, one or more of the catheters comprises a mechanism for occluding the inflow port or outflow port of the heart pump. For example, FIG. 2A depicts an exemplary catheter 10 comprising an inflatable region 20 on the outer surface of catheter 10. Inflatable region 20 may be located anywhere along the length of catheter 10. In one embodiment, inflatable region 20 is located at or near the distal portion of catheter 10. Inflatable region 20 comprises an inflatable balloon 25, which when inflated serves to increase the outer diameter of inflatable region 20 (FIG. 2B). Thus, when catheter 10 is inserted into a vessel (e.g., the inflow port or outflow port of a heart pump) balloon 25 may be inflated which increases the outer diameter of inflatable region 20 to the size of the vessel, thereby occluding the vessel. Balloon 25 may be manufactured of any suitable biocompatible material, including, but not limited to, plastics such as PVC, PET, nylon, silastic, silicone, and the like. In certain embodiments, catheter 10 comprises an inflation lumen in communication with inflatable region 20, to allow for inflation of balloon 25 via a controlled delivery of a fluid, gas, and the like.

Figure 2:
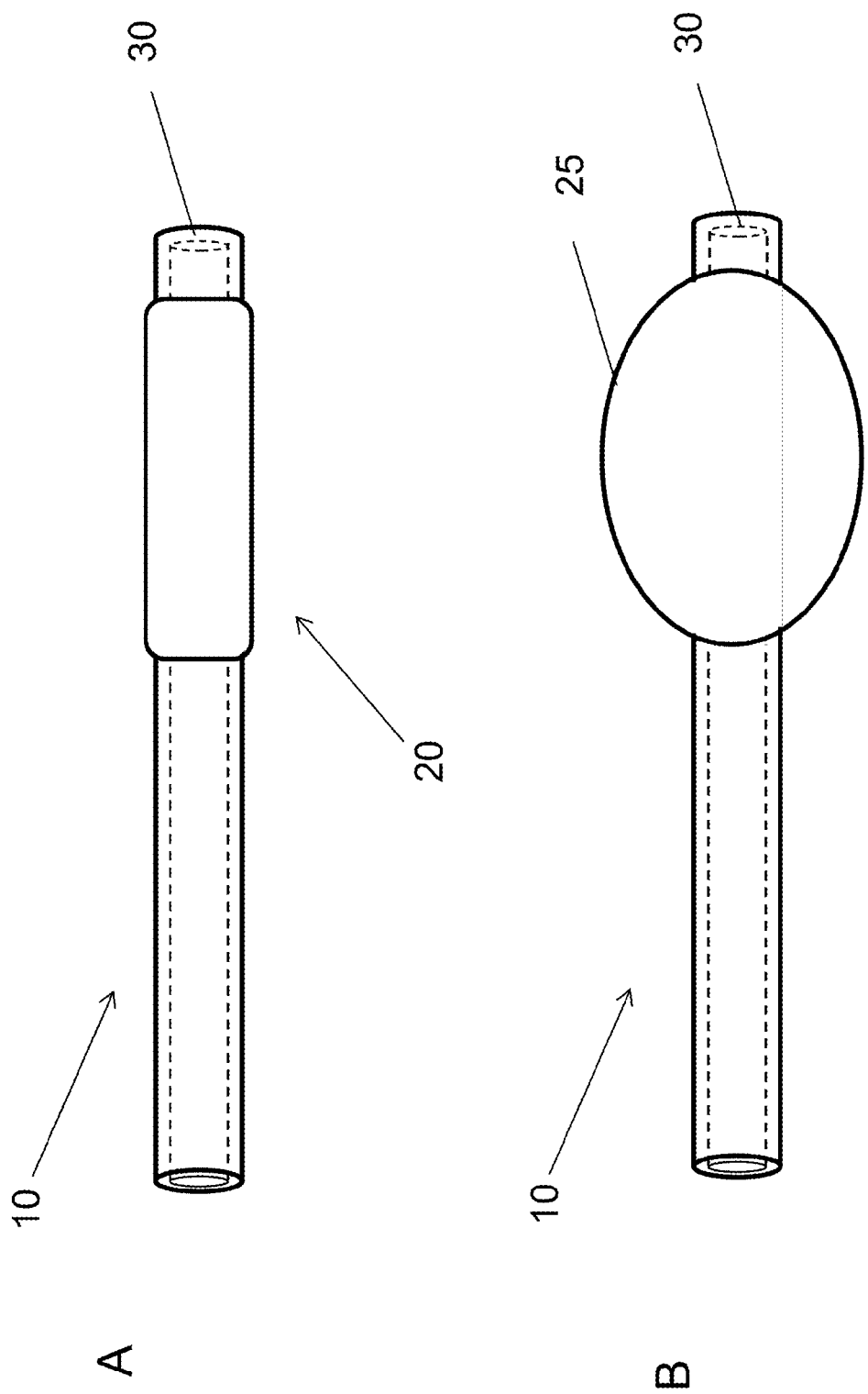
FIG. 2, comprising

As seen in FIG. 2, catheter 10 comprises an inner lumen 30, which forms a hollow passageway in the entire length of catheter 10. Inner lumen 30 can be used for the passage and delivery of additional system components to the heart or heart pump. For example, in one embodiment, additional system components are delivered through inner lumen 30 into an inner chamber of the heart pump. Inner lumen 30 may be of any standard lumen size known in the art. In one embodiment, lumen 30 has a diameter of about 0.5 mm to about 10 mm.

In certain embodiments, the proximal end of catheter 10 is configured for connection to a hub or handle, used by a clinician for the manipulation of catheter 10, balloon 25, and other system components described elsewhere herein.

In some embodiments, the device and system of the invention comprises a scope (i.e., endoscope, optical fiber scope, etc.) for viewing the heart or interior of the heart pump. In certain embodiments, the scope is able to be guided to the heart or the interior of the heart pump through an inner lumen of a catheter. In certain embodiments the scope has a diameter of about 3 mm to about 4 mm. In certain embodiments, the scope has a length of about 50 cm to about 200 cm.

Figure 3:
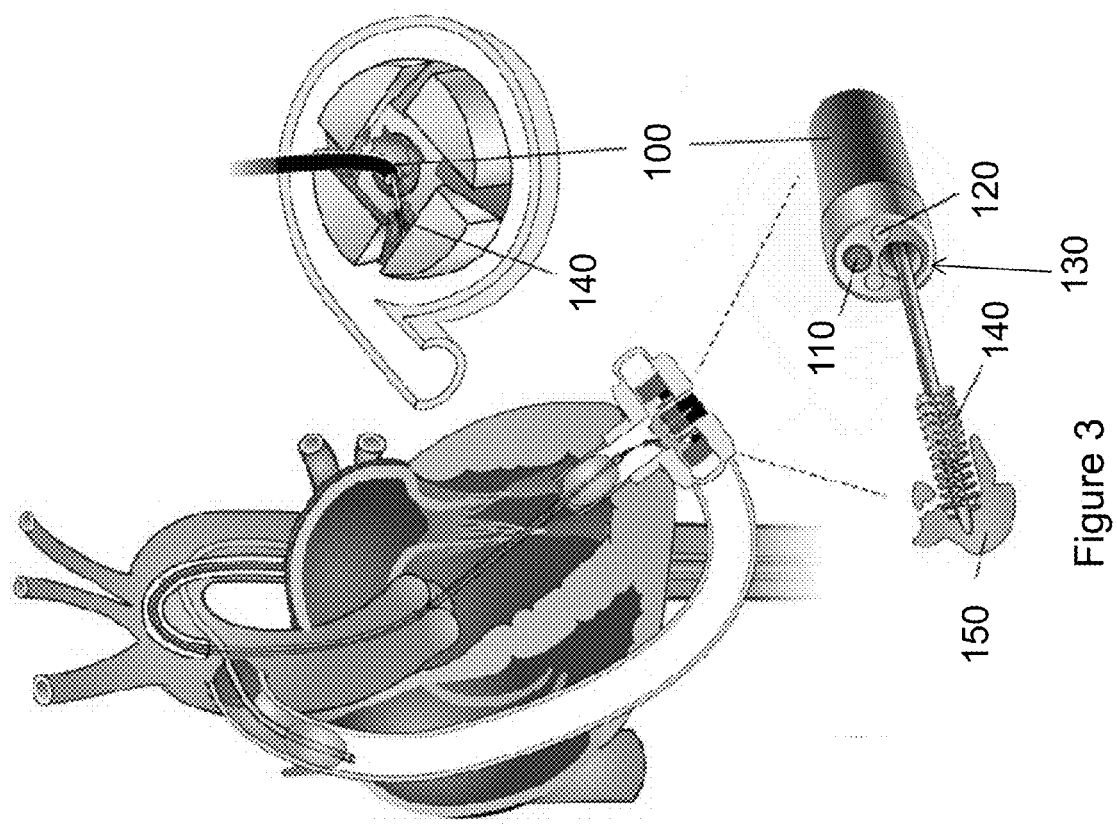
FIG. 3 depicts the placement of an exemplary scope through the lumen of a catheter to inspect the interior chamber of a heart pump, as well as close-up views of the scope within the pump. The scope comprises a working channel in which a brush is passed through to mechanically disrupt blood clots within the pump.

FIG. 3, depicts an exemplary scope 100, comprising lens 110 and light 120, positioned at the distal tip of scope 100. In certain embodiments, scope 100 is able to be guided to the heart or the interior of the heart pump through inner lumen 30 of catheter 10. In some embodiments, scope 100 comprises a working channel 130 forming a hollow passageway through the entire length of scope 100. In some embodiments, working channel 130 allows passage of additional components, including, but not limited to brushes, probes, fluid delivery devices, and additional scopes to the heart or the interior of the heart pump. In one embodiment, working channel 130 allows passage of components having a diameter as small as 0.4 mm. For example, FIG. 3 depicts scope 100 with a brush 140 passed through working channel 130. In some embodiments, brush 140 is used to remove blot clot 150 and/or clean components of the heart pump, including, but not limited to the impeller, rotor, and the like.

Figure 4:
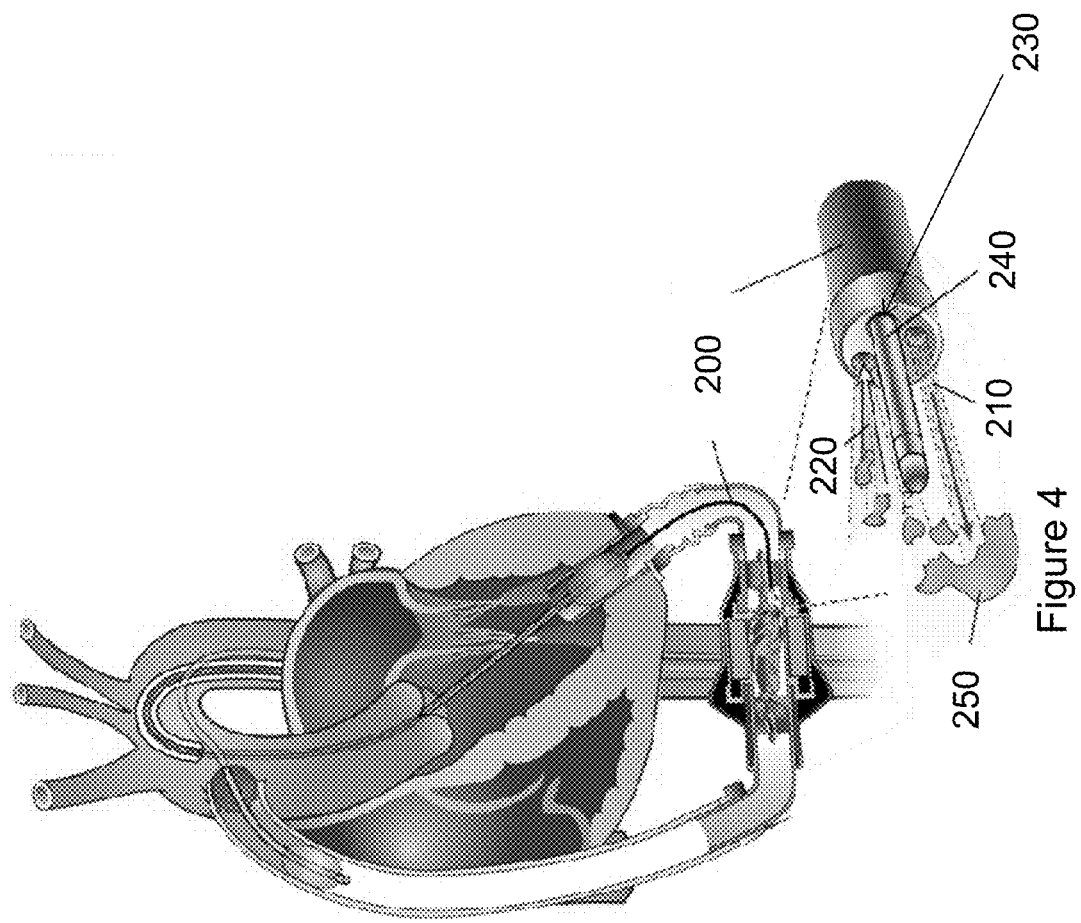
FIG. 4 depicts the placement of a fluid delivery device through the lumen of a catheter into the chamber of a heart pump, as well as a close-up view of the device. The device comprises a working channel in which a probe is passed through. The delivery of fluid and/or actions of the probe promotes disruption of blood clots within the pump.
Figure 7:
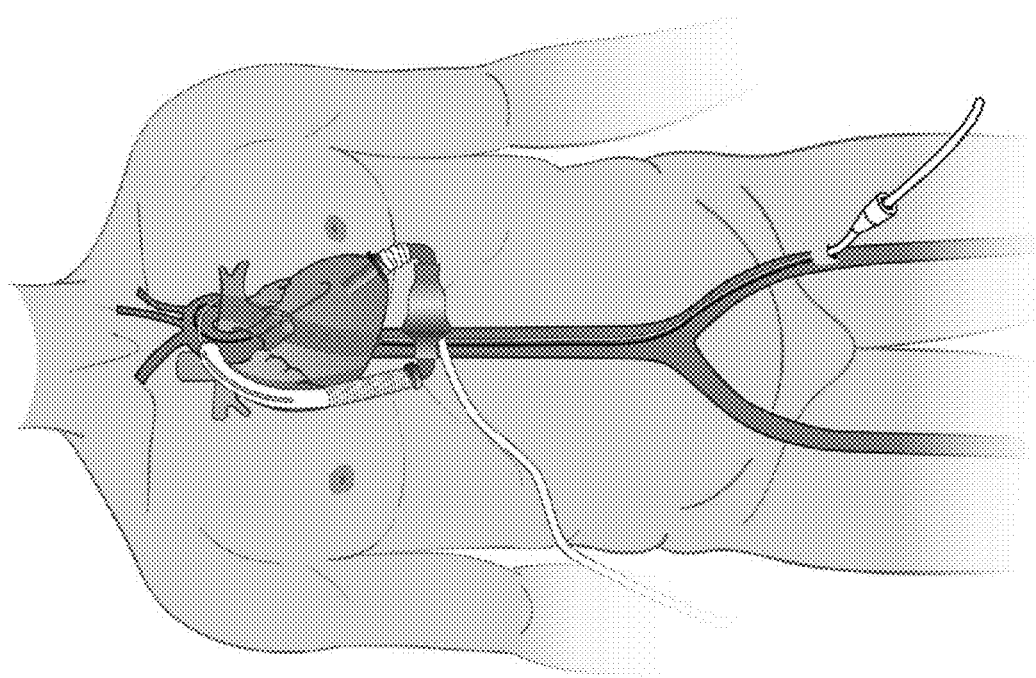
FIG. 7 depicts the insertion and guidance of catheters to the inflow port and/or outflow port of an implanted heart pump.

In one embodiment, the system of the invention comprises a fluid delivery device to deliver a fluid to the heart or the interior of the heart pump. For example, FIG. 4 depicts an exemplary fluid delivery device 200. In one embodiment, device 200 comprises at least one opening at its distal end for the delivery and/or suction of fluid. For example, FIG. 7 shows device 200 comprising opening 210 for delivery of a fluid and opening 220 for the suction of fluid. In certain embodiments, device 200 is able to be guided to the heart or the interior of the heart pump through inner lumen 30 of catheter 10. In one embodiment, device 200 is able to be guided to the heart or the interior of the heart pump through working channel 110 of scope 100.

In some embodiments, device 200 comprises a working channel 230 forming a hollow passageway through the entire length of device 200. In some embodiments, working channel 230 allows passage of additional components, including, but not limited to brushes, probes, scopes, and/or additional fluid delivery devices to the heart or the interior of the heart pump. In one embodiment, working channel 230 allows passage of components having a diameter as small as 0.4 mm.

As depicted in FIG. 4, in certain embodiments, probe 240 is passed through working channel 230 of device 200. In one embodiment, probe 240 uses ultrasonic or laser means to fracture a blood clot 250 that may be formed in the heart pump. In another embodiment, probe 240 is integrated into a delivered scope or fluid delivery device. In another embodiment, probe 240 is a stand-alone component delivered to the heart or the interior of the heart pump via inner lumen 30 of catheter 10, or alternatively, via working channel 130 of scope 100.

In one embodiment, the system comprises one or more catheters comprising one or more thermistors to measure the temperature of the pumped blood. For example, in one aspect of the invention, as described fully elsewhere herein, the system is used to measure the output of the implanted heart pump and/or native heart, by measuring the thermodilution of an injected bolus of fluid. Thus the catheter of the invention may comprise an integrated thermistor at or near the external surface of the catheter. In one embodiment, the thermistor is positioned at or near the distal tip of the catheter. In one embodiment, the thermistor is positioned proximal to the distal tip. In certain aspects, the catheter comprises a first thermistor at or near the distal tip and a second thermistor positioned proximally, downstream of the flow of blood.

In certain embodiments, the system comprises closure devices that are able to be placed at the inflow port and outflow port of the pump to block flow into and out of the pump for mid-term or permanent exclusion of the heart pump. Such closure devices may be used when it is determined that native heart function is adequate to support sufficient blood supply to the entire body, and that the use of the heart pump is no longer necessary.

Figure 5:
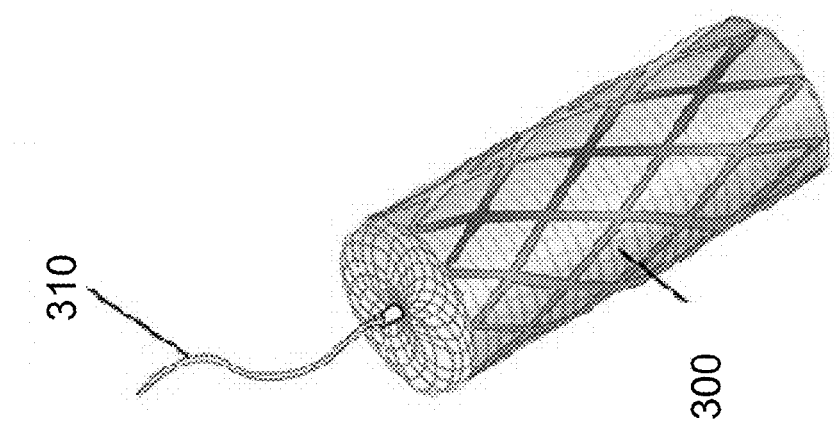
FIG. 5 depicts an exemplary closure device of the system of the present invention for mid-term or permanent occlusion of the inflow port and outflow port of the pump to provide mid-term or permanent exclusion of the heart pump from blood flow.

An exemplary closure device 300 is depicted in FIG. 5. In one embodiment, closure device 300 is deformable such that it completely occludes flow when inserted into a vessel or into the inflow or outflow of a heart pump. Closure device 300 can be made from any suitable biocompatible material including titanium, stainless steel, nitinol, polyethylene terephthalate, polyether ether ketone, polyurethane, graphene, and the like. In certain embodiments, closure device 300 comprises polyethylene terephthalate and wire. In one embodiment, the closure device comprises one or more manipulation structures 310 that allow for a user to manipulate the placement of device 300 and/or assist in removal of device 300 from its implanted position. Manipulation structures 310 may comprise, for example, one or more wires, strings, knobs, ridges, cavities, and the like. For example, protrusions 310 of device 300 may comprise one or more pull-strings positioned at the proximal end of device 300, where the pull-strings may be grasped and manipulated using conventional instrumentation.

In one embodiment, the system comprises an external control and monitoring unit comprising hardware and software to view, monitor, and control the maintenance and manipulation of heart pump function. For example, the one or more catheters or other system components may be wired or wirelessly connected to the external control and monitoring unit to provide a clinician with real-time data regarding system function. The external control and monitoring unit can thus be used to visualize the interior of the heart and heart pump, via an inserted scope, control fluid delivery, calculate output, control probe function, and the like.

The external control and monitoring unit includes a graphical user interface (GUI) for modulating the system or system components and for displaying information regarding the historical or real-time functionality of the heart pump and/or the subject's cardiac function. In certain embodiments, wireless communication for information transfer to and from system components and the external control and monitoring unit may be via a wide area network and may form part of any suitable networked system understood by those having ordinary skill in the art for communication of data to additional computing devices, such as, for example, an open, wide area network (e.g., the internet), an electronic network, an optical network, a wireless network, a physically secure network or virtual private network, and any combinations thereof. Such an expanded network may also include any intermediate nodes, such as gateways, routers, bridges, internet service provider networks, public-switched telephone networks, proxy servers, firewalls, and the like, such that the network may be suitable for the transmission of information items and other data throughout the system.

As would be understood by those skilled in the art, external control and monitoring unit may be wirelessly connected to the expanded network through, for example, a wireless modem, wireless router, wireless bridge, and the like. Additionally, the software platform of the system may utilize any conventional operating platform or combination of platforms (Windows, Mac OS, Unix, Linux, Android, etc.) and may utilize any conventional networking and communications software as would be understood by those skilled in the art.

To protect data, an encryption standard may be used to protect files from unauthorized interception over the network. Any encryption standard or authentication method as may be understood by those having ordinary skill in the art may be used at any point in the system of the present invention. For example, encryption may be accomplished by encrypting an output file by using a Secure Socket Layer (SSL) with dual key encryption. Additionally, the system may limit data manipulation, or information access. Access or use restrictions may be implemented for users at any level. Such restrictions may include, for example, the assignment of user names and passwords that allow the use of the present invention, or the selection of one or more data types that the subservient user is allowed to view or manipulate.

In certain embodiments the network provides for telemetric data transfer from the system components to the external control and monitoring unit, and vice versa. For example, data transfer can be made via any wireless communication and may include any wireless based technology, including, but not limited to radio signals, near field communication systems, hypersonic signal, infrared systems, cellular signals, GSM, and the like. In some embodiments, data transfer is conducted without the use of a specific network. Rather, in certain embodiments, data is directly transferred to and from the controller and external control unit via systems described above.

The external control and monitoring unit may be any computing device including, desktop or mobile devices, laptops, desktops, tablets, smartphones or other wireless digital/cellular phones, wrist watches, televisions or other thin client devices as would be understood by those skilled in the art. The computing devices may include at least one processor, standard input and output devices, as well as all hardware and software typically found on computing devices for storing data and running programs, and for sending and receiving data over a network, if needed.

The software may include a software framework or architecture that optimizes ease of use of at least one existing software platform, and that may also extend the capabilities of at least one existing software platform. The software provides applications accessible to one or more users (e.g. patient, clinician, etc.) to perform one or more functions. Such applications may be available at the same location as the user, or at a location remote from the user. Each application may provide a graphical user interface (GUI) for ease of interaction by the user with information resident in the system. A GUI may be specific to a user, set of users, or type of user, or may be the same for all users or a selected subset of users. The system software may also provide a master GUI set that allows a user to select or interact with GUIs of one or more other applications, or that allows a user to simultaneously access a variety of information otherwise available through any portion of the system. Presentation of data through the software may be in any sort and number of selectable formats. For example, a multi-layer format may be used, wherein additional information is available by viewing successively lower layers of presented information. Such layers may be made available by the use of drop down menus, tabbed pseudo manila folder files, or other layering techniques understood by those skilled in the art.

The software may also include standard reporting mechanisms, such as generating a printable results report, or an electronic results report that can be transmitted to any communicatively connected computing device, such as a generated email message or file attachment. Likewise, particular results of the aforementioned system can trigger an alert signal, such as the generation of an alert email, text or phone call, to alert a patient, doctor, nurse, emergency medical technicians, or other health care provider of the particular results.

Figure 6:
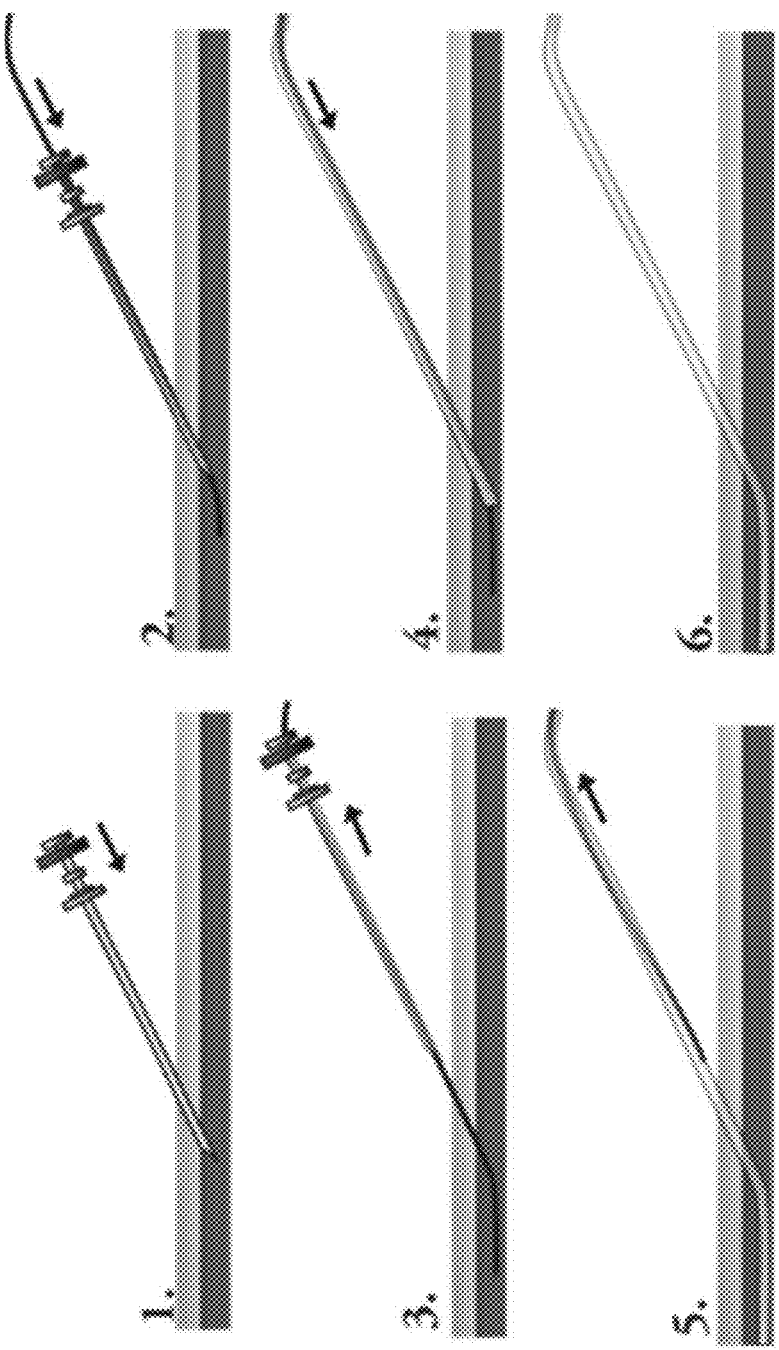
FIG. 6 depicts an exemplary protocol for inserting a catheter into a blood vessel of a subject.
Figure 8:
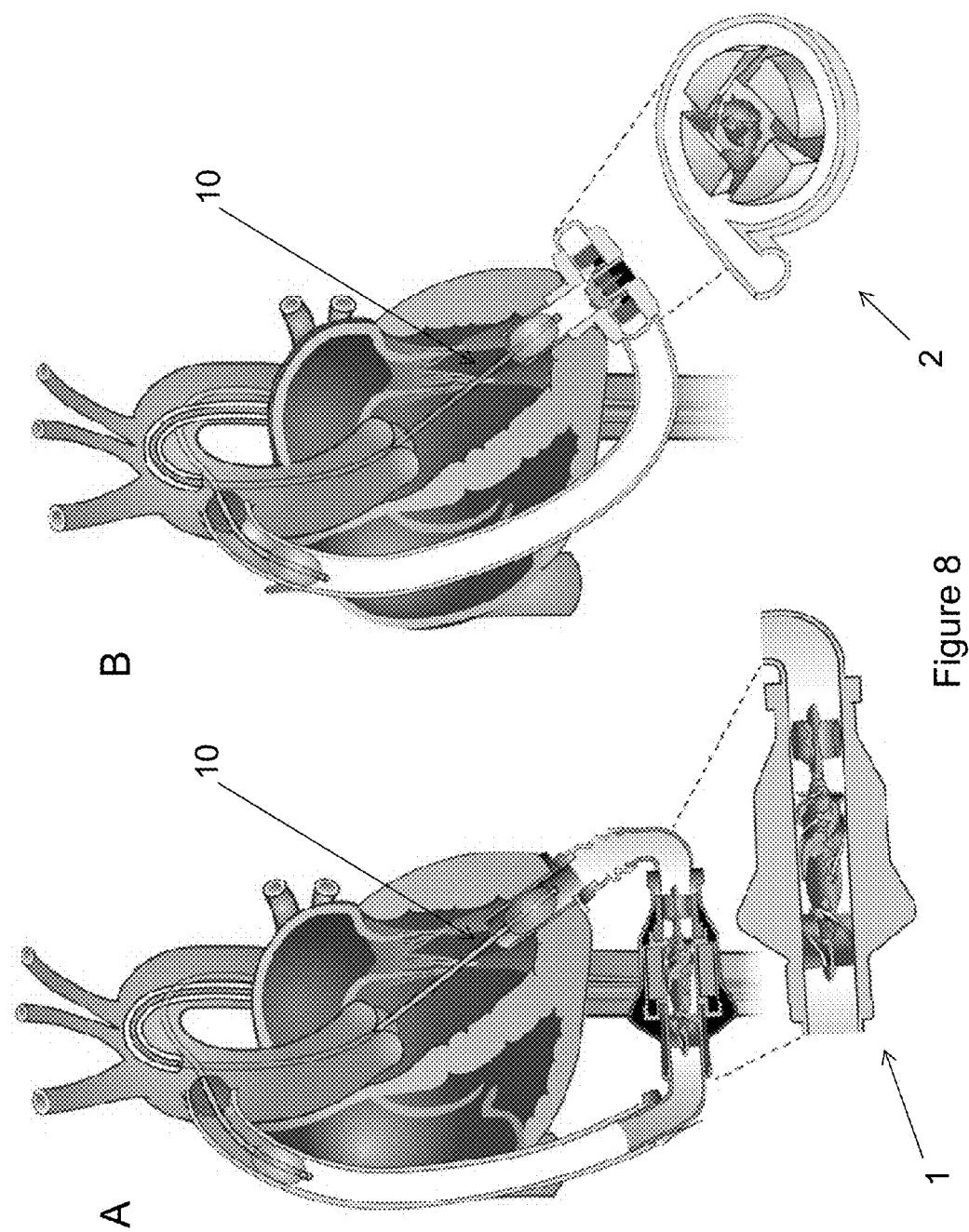
FIG. 8, comprising

The present invention provides method of interrogating, inspecting and manipulating heart pump function in situ. In certain embodiments, the method of the invention comprises guiding one or more catheters into the inflow port or outflow port of the heart pump. Guiding of the catheters to the heart pump can be done by any suitable method known in the art. For example, in one embodiment, the method comprises using the Seldinger technique (FIG. 6) for the insertion of a sheath into a blood vessel of a subject whose heart pump is being examined or manipulated. The inserted sheath then serves as an access point allowing for the introduction of one or more catheters, scopes, fluid delivery devices, and the like, into the blood vessel. The access point, where the sheath is inserted, may be located in any suitable location. For example, in certain embodiments, the access point for the sheath, catheter, or other components is the femoral artery in the subject's groin or in the radial artery in the subject's wrist. However, any suitable access point which provides access to the heart or heart pump may be used. As shown in FIG. 7, a small steerable catheter is passed from the femoral artery and threaded into the ascending aorta to the left ventricle. This catheter can then access the inflow port of an implanted heart pump. In certain embodiments, the catheter is a steerable catheter with a steering handle and bendable tip. However, any suitable catheter that may be steered to the heart or heart pump may be used. In certain embodiments, another similar catheter is guided to the outflow port of the heart pump. In one embodiment, the method comprises placing the catheter at the inflow port or outflow port of the pump, and then inflating a balloon at the distal end of the catheter, which physically occludes blood flow into or out of the pump. For example, FIG. 8 depicts catheters 10 positioned at the inflow port and the outflow port of pump 1 (FIG. 8A) and pump 2 (FIG. 8B), with the balloons of both catheters 10 inflated. This allows for complete isolation of the heart pump, and excludes the heart pump from the blood flow path.

In some embodiments, the methods of the invention comprise inserting additional system components into the heart or heart pump. For example, as described elsewhere herein, in certain embodiments the inserted catheter comprises an inner lumen through which an additional system component may be inserted and guided to the heart or the interior of the heart pump. Such additional components include, but are not limited to, fluid delivery devices, probes, scopes, and the like (FIG. 3 and FIG. 4).

In certain embodiments, the heart pump is turned off while the additional system components are inserted into the inflow, outflow, and/or interior of the pump.

In one embodiment, the method of the invention uses the one or more inserted catheters to monitor heart pump function and to diagnose malfunction. For example, the development of blood clots or thrombosis within the heart pump can cause decreased flow or potentially may completely occlude blood flow. In one embodiment, the method of the invention allows for inspection of the interior of the heart pump to detect the presence of blood clot formation. The methods may be performed on a routine basis for all subjects with implanted heart pumps. In certain embodiments, the methods are performed on subjects who are determined to be at increased risk for the development of clots within the implanted pump.

Figure 12:
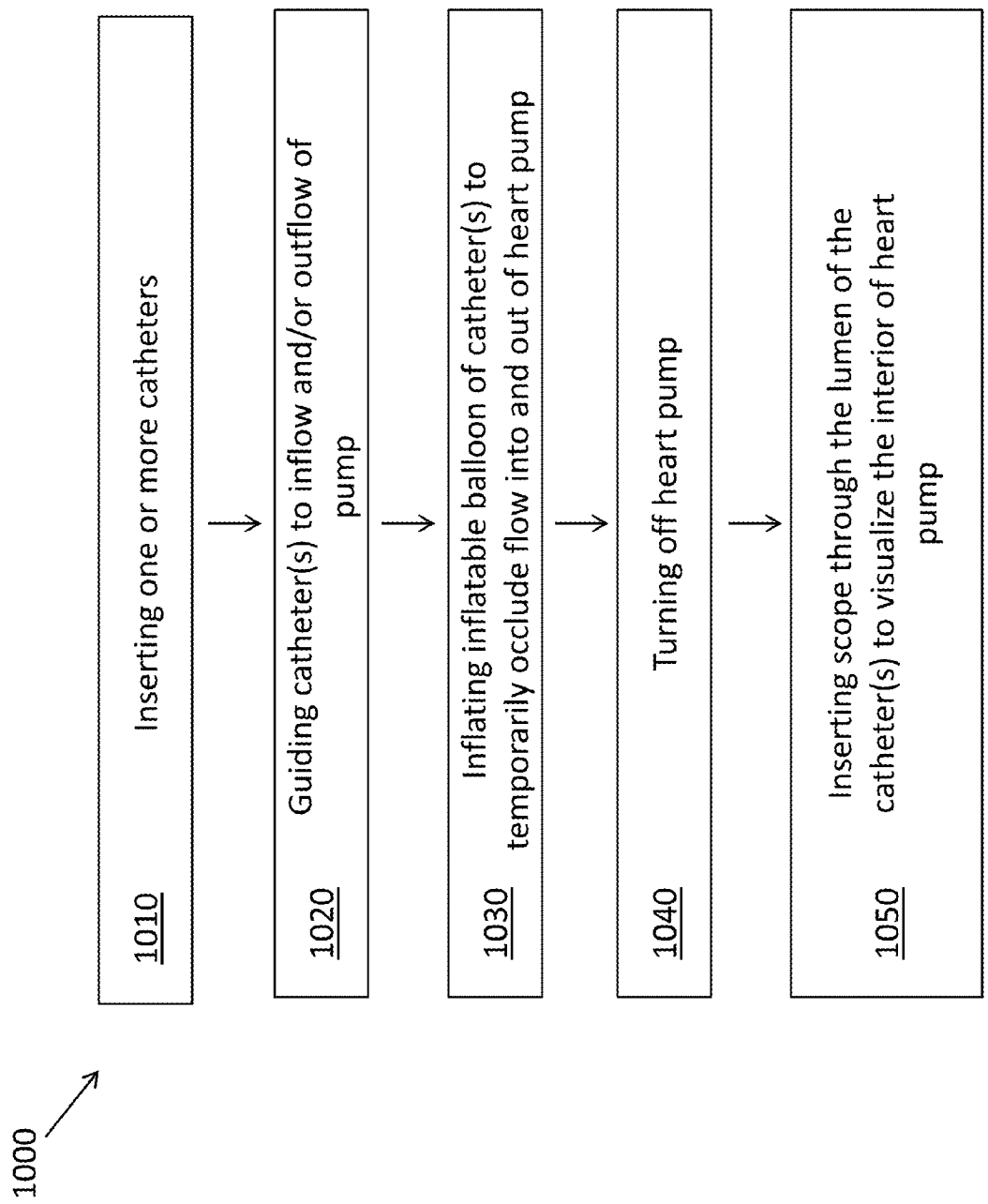
FIG. 12 depicts a flow chart illustrating an exemplary method for inspection of the interior of the heart pump.

FIG. 12 depicts a flow chart illustrating an exemplary method 1000 for inspection of the interior of the heart pump. Method 1000 comprises inserting one or more catheters into the patient 1010, and guiding of the one or more catheters to the inflow and/or outflow of the heart pump 1020. In certain embodiments, the catheter comprises an inflatable balloon on the outer surface of the catheter. Inflating the balloon 1030 then occludes the inflow port or outflow port, preventing blood from entering or exiting. In one embodiment, method 1000 comprises turning off of the pump 1040, to allow for safe insertion of a scope into the pump. The turning off of pump 1040 may be done before or after guiding of the catheters 1020 and/or inflation of the balloon 1030. In certain embodiments, method 100 comprises delivery of a scope to the heart pump 1050, via the inner lumen of the catheter, to provide visualization of the interior of the heart pump to a physician, clinician, or other health care provider (FIG. 3).

In one embodiment, the method of the invention comprises cleaning of the interior of the heart pump. For example, in certain embodiments, the method comprises removing blood clots and/or preventing the formation of future blood clots in the heart pump.

In one embodiment, the method comprises cleaning of the interior of the heart pump using a brush that may be guided to the interior of the heart pump via the inner lumen of the catheter or alternatively via a working channel of a scope or other system component, as described elsewhere herein (FIG. 3).

Figure 9:
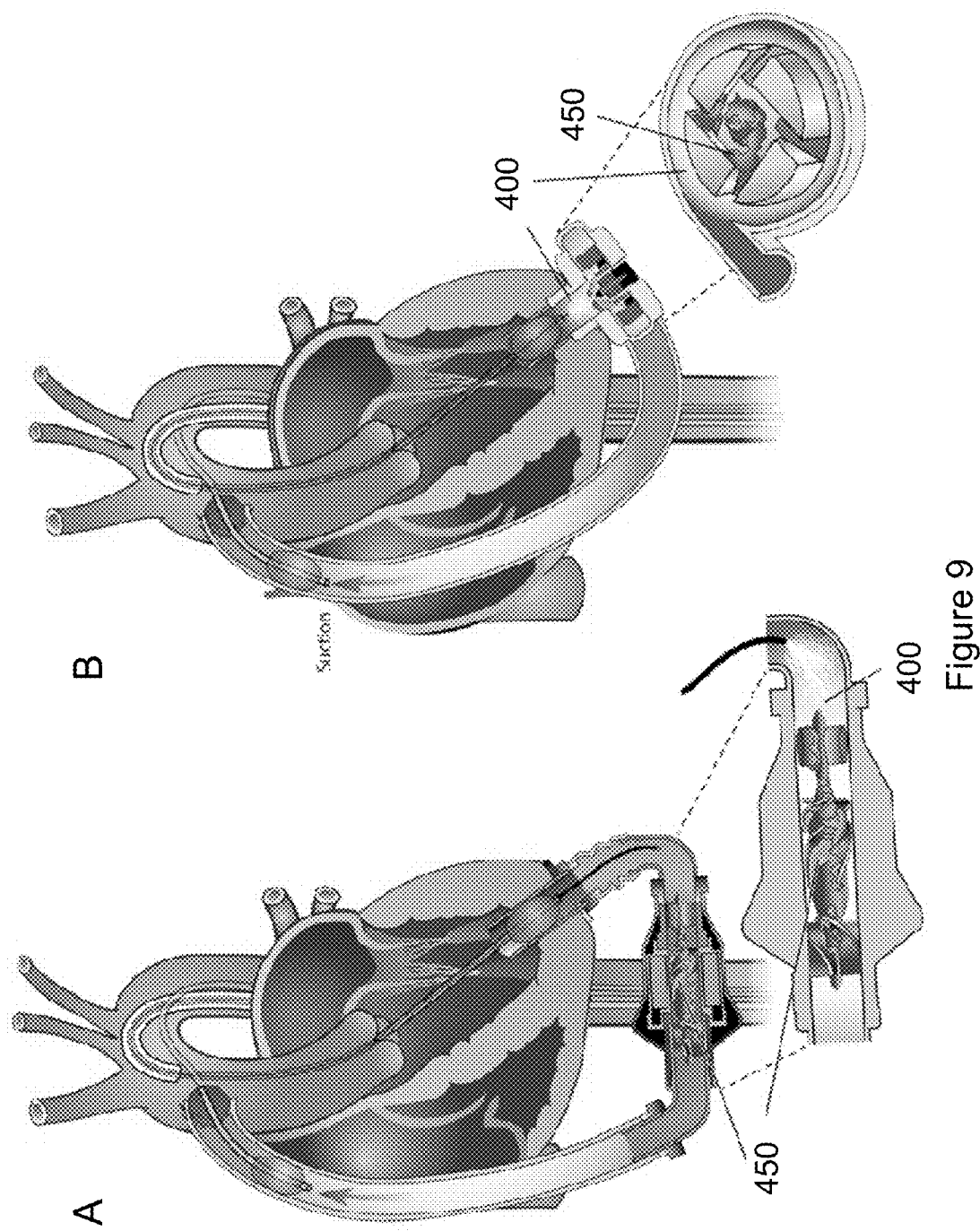
FIG. 9, comprising

In one embodiment, the method comprises delivering a solution to the interior of the heart pump to break up blood clots and/or to washout the pump components. In one embodiment, a solution is delivered through the inner lumen of a catheter positioned at either the inflow or outflow of the pump. In one embodiment, a fluid delivery device is delivered to the interior of the heart pump, via the inner lumen of the catheter or alternatively via the working chamber of a scope or other system component, as described elsewhere herein, to deliver a reagent or solution to the interior of the heart pump. For example, FIG. 9 depicts the delivery of a solution 400 to the interior of a heart pump in order to remove or prevent the accumulation of blood clots 450 within the pump. In one embodiment, the method comprises delivery of saline or other buffer to wash out the heart pump. In one embodiment, the method comprises delivery a solution 400 comprising an anticoagulant to the interior of the heart pump. Any suitable anticoagulant may be used. For example, in one embodiment, the method comprises delivery of a solution 400 comprising heparin, tissue plasminogen activator (tPa), streptokinase, collagenase, proteases, proteolytic agents, superhydrophobic agents, or analogs thereof, to the interior of the heart pump. In certain embodiments, the solution is delivered via a high pressure or high velocity stream.

In some embodiments, the method comprises fracturing of a clot by administering ultrasonic or laser pulses to the clot. In one embodiment, the method comprises using a suction to collect or remove delivered fluid, clot residue, and the like from the interior of the pump (FIG. 4 and FIG. 9). In one embodiment, suctioning of fluid and clot residue may be done via a second catheter positioned at or near the outflow of the pump (FIG. 9). In another embodiment, a fluid delivery device comprises an opening or lumen for the suctioning of delivered fluid and clot residue (FIG. 4).

Figure 13:
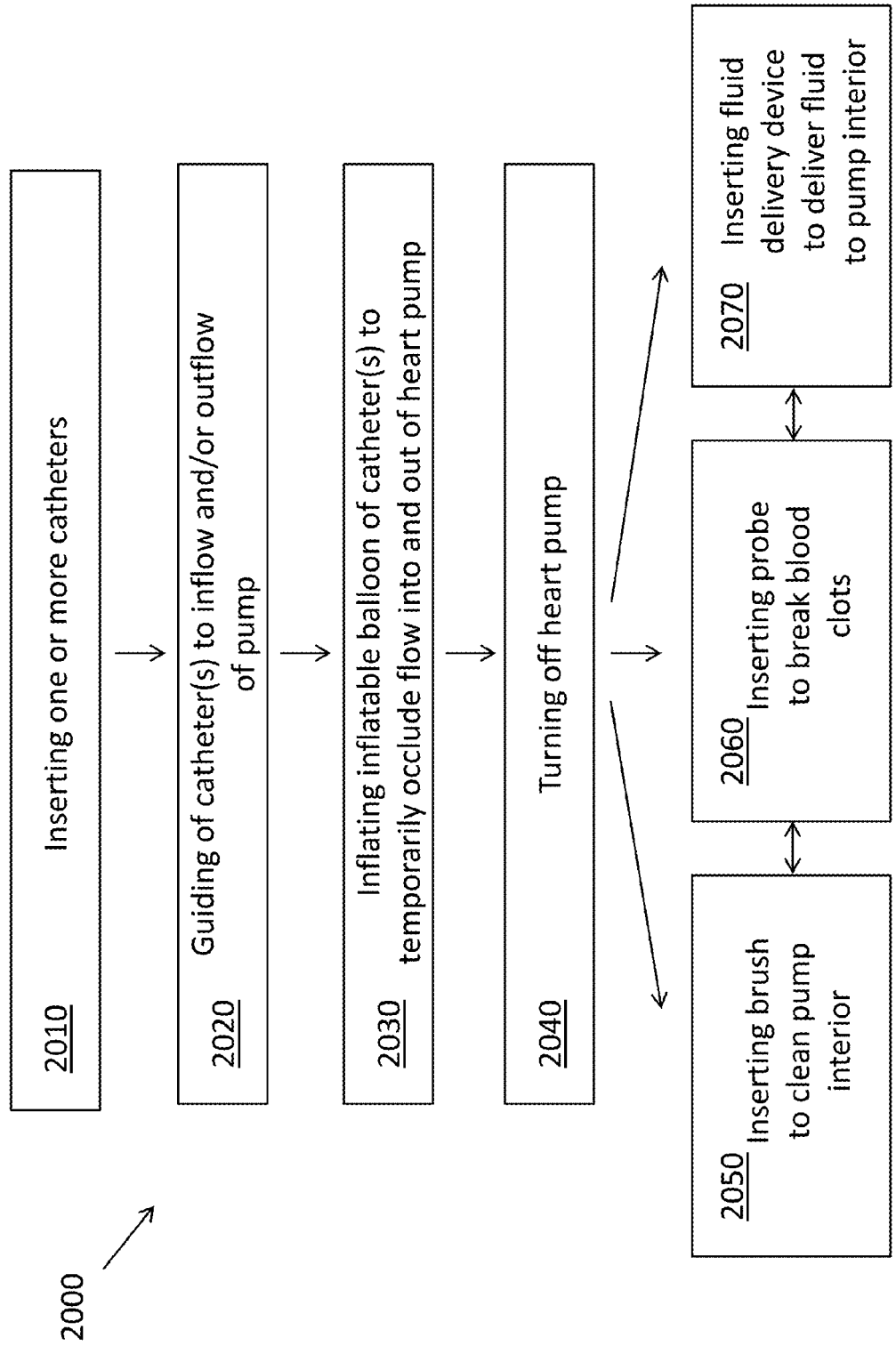
FIG. 13 depicts a flow chart illustrating an exemplary method for cleaning or maintenance of the interior of the heart pump.

FIG. 13 depicts a flow chart illustrating an exemplary method 2000 for cleaning or maintenance of the interior of the heart pump. Method 2000 comprises inserting one or more catheters into the patient 2010, and guiding of the one or more catheters to the inflow and/or outflow of the heart pump 2020. In certain embodiments, the catheter comprises an inflatable balloon on the outer surface of the catheter. Inflating the balloon 2030 then occludes the inflow port or outflow port, preventing blood from entering or exiting. In one embodiment, method 2000 comprises turning off of the pump 2040, to allow for safe insertion of additional system components (e.g. brush, fluid delivery device, etc.) into the pump. The turning off of pump 2040 may be done before or after guiding of the catheters 2020 and/or inflation of the balloon 2030. In one embodiment, method 2000 comprises inserting a brush into the pump interior 2050, which allows of the cleaning of interior pump components. In one embodiment, method 2000 comprises inserting a probe into the pump interior 2060, which may aid in breaking of resident blood clots within the pump. In one embodiment, method 2000 comprises inserting a fluid delivery device into the pump interior 2070, which allows for the delivery of a fluid to wash out the pump interior, aid in breaking resident blood clots, and/or prevent the formation of future clots. It should be appreciated that one or more of steps 2050, 2060 and 2070 may be performed in accordance with the claimed method, or alternatively, any other cleaning and/or maintenance step may be performed, as desired.

Figure 10:
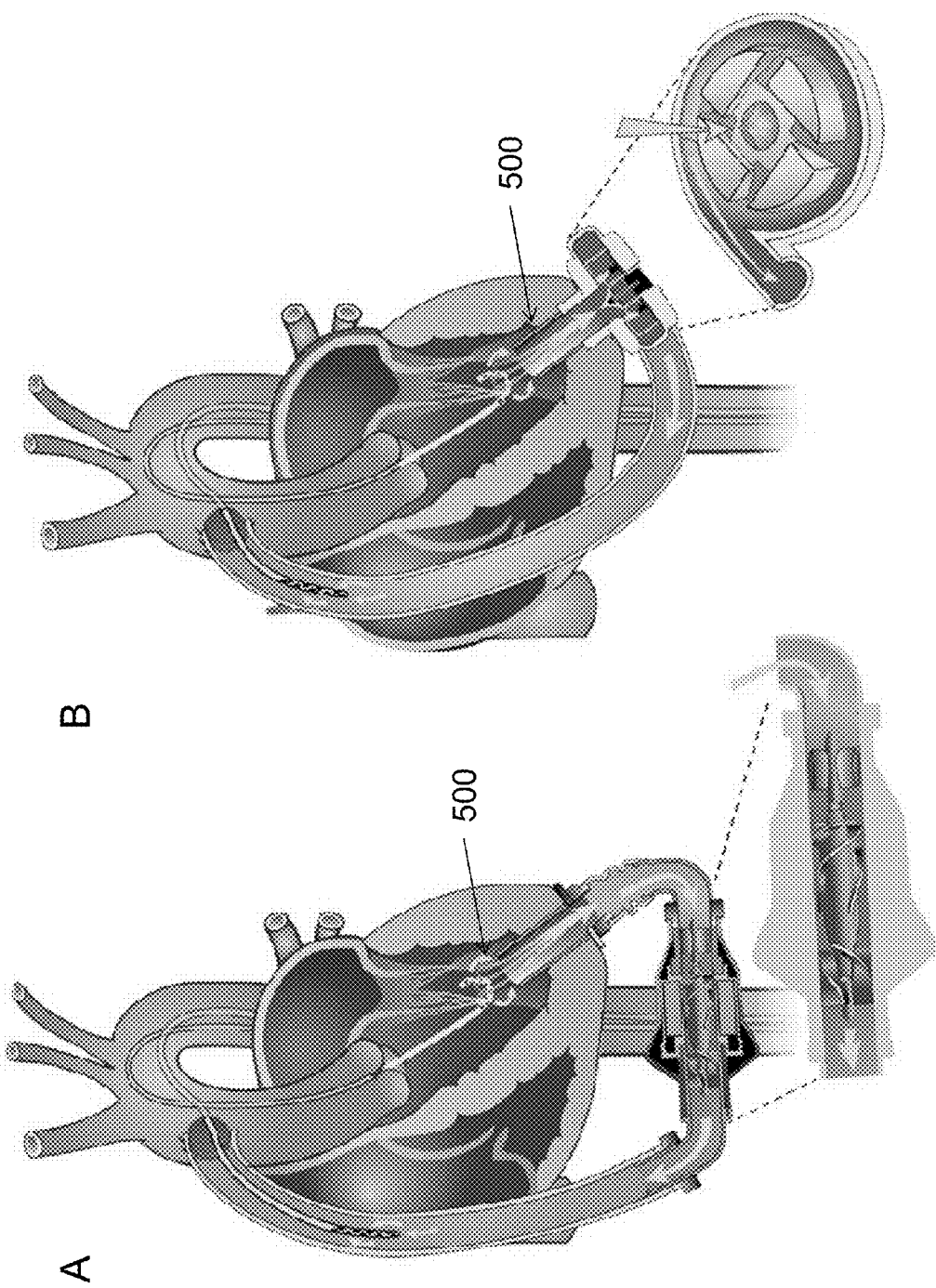
FIG. 10A and FIG. 10B, depicts the measurement of blood flow and cardiac output from an implanted axial pump (FIG. 10A) and centrifugal pump (FIG. 10B) by injecting a fluid at the inflow of the pump and measuring the temperature of the pumped blood at the outflow.

In one embodiment, the invention provides for systems and methods for directly measuring heart pump or cardiac output by measuring the flow produced by the pump or native heart. In one embodiment, the method comprises inserting a catheter into or near the outflow port of the implanted heart pump. In one embodiment, the method comprises inserting a catheter into or near the inflow port of the implanted heart pump. As described elsewhere herein, insertion of the catheter may be performed by any suitable method known in the art. Flow measurement may be computed using a variety of different methods, including but not limited to, indicator dye dilution, thermo dilution, Doppler flow measurement, and ultrasonic flow measurement. For example, in one embodiment, the method comprises delivery of a fluid and measuring a characteristic of the fluid at a known distance from the delivery site. In one embodiment, the characteristic of the fluid is the presence, amount, and/or concentration of a dye or other indicator substance, such as inulin, methylene blue, lithium chloride, or the like. In one embodiment, the characteristic of the fluid is the presence, amount, and/or concentration of a gas, such as oxygen, carbon dioxide, or their radiolabeled derivatives. In certain embodiments, the characteristic of the fluid is the temperature. For example, measuring a drop in fluid temperature from points at a known distance allows for the direct computation of the flow mediated by the pump. A skilled artisan would appreciate that the delivery site and measurement points used in the calculation can be located anywhere in the vicinity of the heart pump and within the pump blood flow. For example, in one embodiment, a fluid is delivered to the blood stream at the outflow port while the temperature of the blood stream is measured at one or more points upstream from the delivery site. In certain embodiments, as depicted in FIG. 10, the method comprises delivery of a fluid 500 to the inflow port of the heart pump. The heart pump pumps blood, comprising the administered fluid, out via the outflow port, where the temperature of the blood stream can be measured. The change in temperature, from the known temperature of the delivered fluid and the measured temperature at the outflow can be used to calculate flow driven by the pump, as described elsewhere herein. Delivery of the fluid may be done by any suitable method known in the art. For example, in one embodiment, the fluid is delivered by a fluid delivery device guided to the delivery site through the inner lumen of an inserted catheter. In certain embodiments the temperature of the delivered fluid is known prior to delivery. In one embodiment, the temperature of the blood stream is measured at the delivery site. Measurement of the temperature of the blood stream can be made by any suitable method known in the art. In certain embodiments, measurement of the temperature of the blood stream is made by a thermistor positioned on an inserted catheter.

Figure 14:
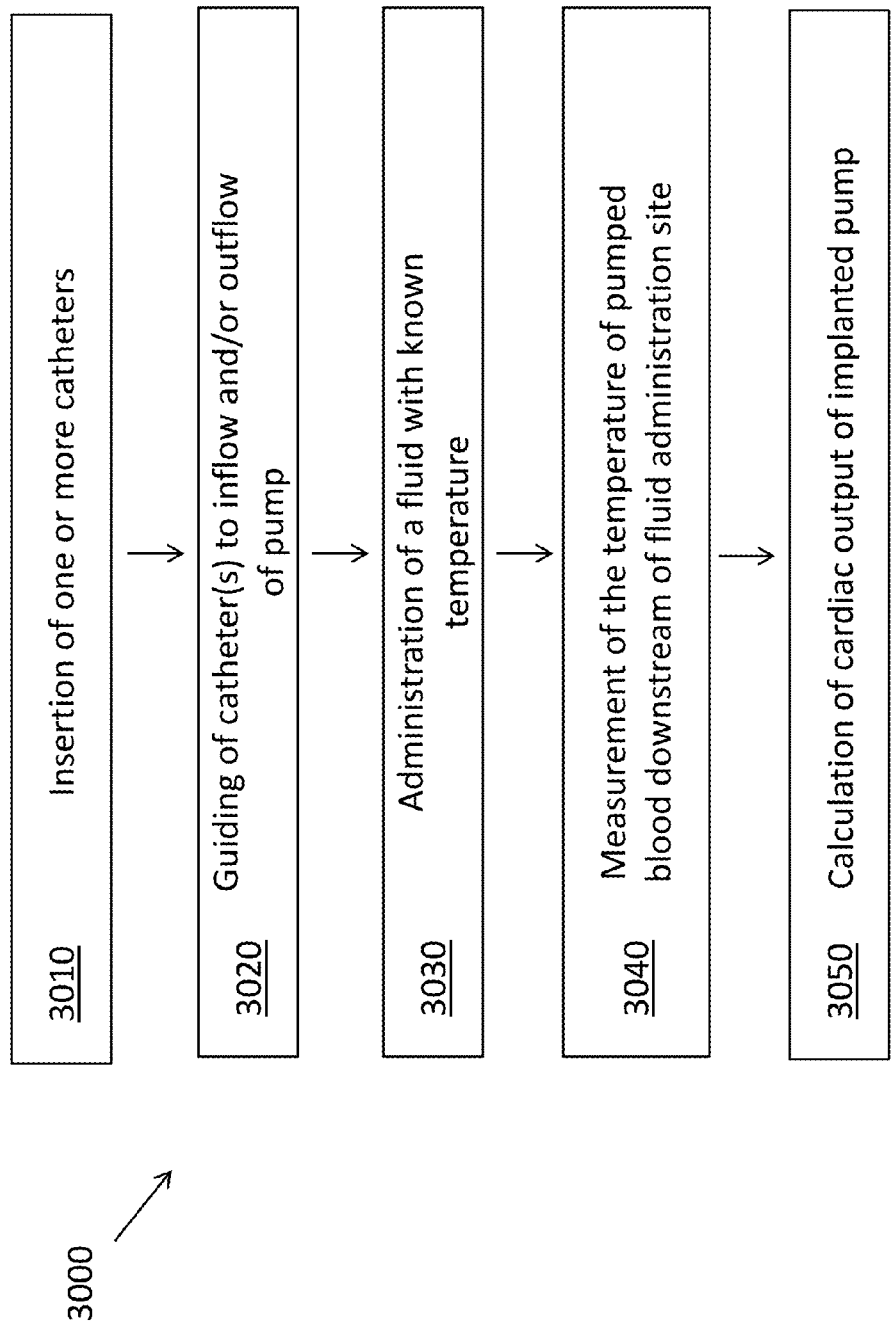
FIG. 14 depicts a flow chart illustrating an exemplary method for measurement of cardiac output of an implanted pump

FIG. 14 depicts a flow chart illustrating an exemplary method 3000 for measurement of cardiac output of an implanted pump. Method 3000 comprises inserting one or more catheters into the patient 3010, and guiding of the one or more catheters to the inflow and/or outflow of the heart pump 3020. In one embodiment, method 3000 comprises administering a fluid with known temperature 3030 to a first location, as described above, and measuring the temperature of pumped blood 3040 at a second location downstream of the first location. In one embodiment, method 3000 comprises calculating of cardiac output 3050 using the change in temperature from the measured blood stream temperature and administered fluid.

In certain embodiments, the method comprises measuring the output of the native heart. For example, in certain embodiments, the method comprises measuring the flow produced by the native heart with an implanted heart pump turned off. In another embodiment, the method comprises measuring the output of a native heart in a patient who does not have an implanted heart pump. That is, the one or more catheters, fluid delivery devices, and the like, described above, may be guided to various sites within the heart or circulatory system in order to measure the flow produced by the heart.

An exemplary thermodilution technique to calculate heart pump or cardiac output, by measuring the temperature of the pumped fluid, is provided below.

Let H be the amount of heat leaving at an instant t $$dH = \rho c (T(t) - T_0) dV \tag{1}$$

Where: $\rho$=density; c=specific heat capacity; T(t)=temperature of fluid at time t; $T_0$=temperature of fluid at time 0; and dV=volume exiting at time t.

Therefore, $$\frac{dH}{dt} = \rho c (T(t) - T_0) \frac{dV}{dt} \tag{2}$$

By substituting Q (flow) for dV/dt and $\Delta T$ for $(T(t)-T_0)$, and integrating:

$$H = \rho c Q \int_0^\infty \Delta T(t) dt \tag{3}$$

The heat of the injectate can be given by:

$$H = \rho_{INJ} c_{INJ} (T_{0INJ} - T_{0F}) V_F \tag{4}$$

Substituting equation 4 into equation 3, and rearranging gives:

$$Q = \frac{\rho_{INJ} c_{INJ} (T_{0INJ} - T_{0F}) V_F}{\rho c \int_0^\infty \Delta T(t) dt} \tag{5}$$

Therefore, the equation used to calculate the average flow from the injection of a bolus of cold fluid is:

$$Q = \frac{\rho_{INJ} c_{INJ}}{\rho_F c_F} \frac{V_{INJ}(T_{0INJ} - T_{0F})}{\int_0^\infty (T_F(t) - T_{0F}) dt} \tag{6}$$

where: Q=Flow; $\rho_{INJ}$=density of injectate; $c_{INJ}$=specific heat capacity of injectate; $\rho_F$=density of fluid; $c_F$=specific heat capacity of fluid; $V_{INJ}$=volume of injectate; $T_{0INJ}$=temperature of injectate at time zero; $T_{0F}$=temperature of fluid at time zero; and $T_F(t)$=instantaneous temperature of fluid.

In one embodiment, the present invention includes a method of monitoring native heart function in a subject with an implanted heart pump. For example, the method comprises occluding the inflow port and outflow port of the heart pump for a period of time, to monitor heart function. In one embodiment, the method comprises guiding a catheter to the inflow port of the heart pump and guiding a second catheter to the outflow port of the heart pump. In certain embodiments, inflation of a balloon on the distal ends of each catheter occludes the flow into and out of the pump, thereby isolating the heart from the pump and excluding the pump from the blood flow loop. In certain embodiments, the method comprises turning the pump off. A physician, clinician, or other health care provider can then use standard techniques and/or methods described herein, to monitor and assess the function of the isolated native heart tissue. Through the isolation of the heart from the pump using the catheter system of the invention, a physician, clinician, or other health care provider can assess the recovery of the native heart tissue or assess the weaning of the heart pump. The present method therefore allows for assessments of native heart tissue without actually having to remove the pump from its implanted position.

In one embodiment, the invention provides methods for in situ temporary, mid-term, or permanent exclusion of a heart pump. The method comprises occluding blood flow into and out of the heart pump with a first occlusion structure positioned at the inflow port and a second occlusion structure positioned at the outflow port. For example, as described elsewhere herein, in certain embodiments, the system comprises catheters with inflatable balloons at the distal end, such that when inflated can occlude the inflow port and outflow port of the pump. This temporary exclusion can be used during maintenance of the pump, removal of clots, measuring heart pump-mediated flow, assessing heart function, and the like.

Figure 11:
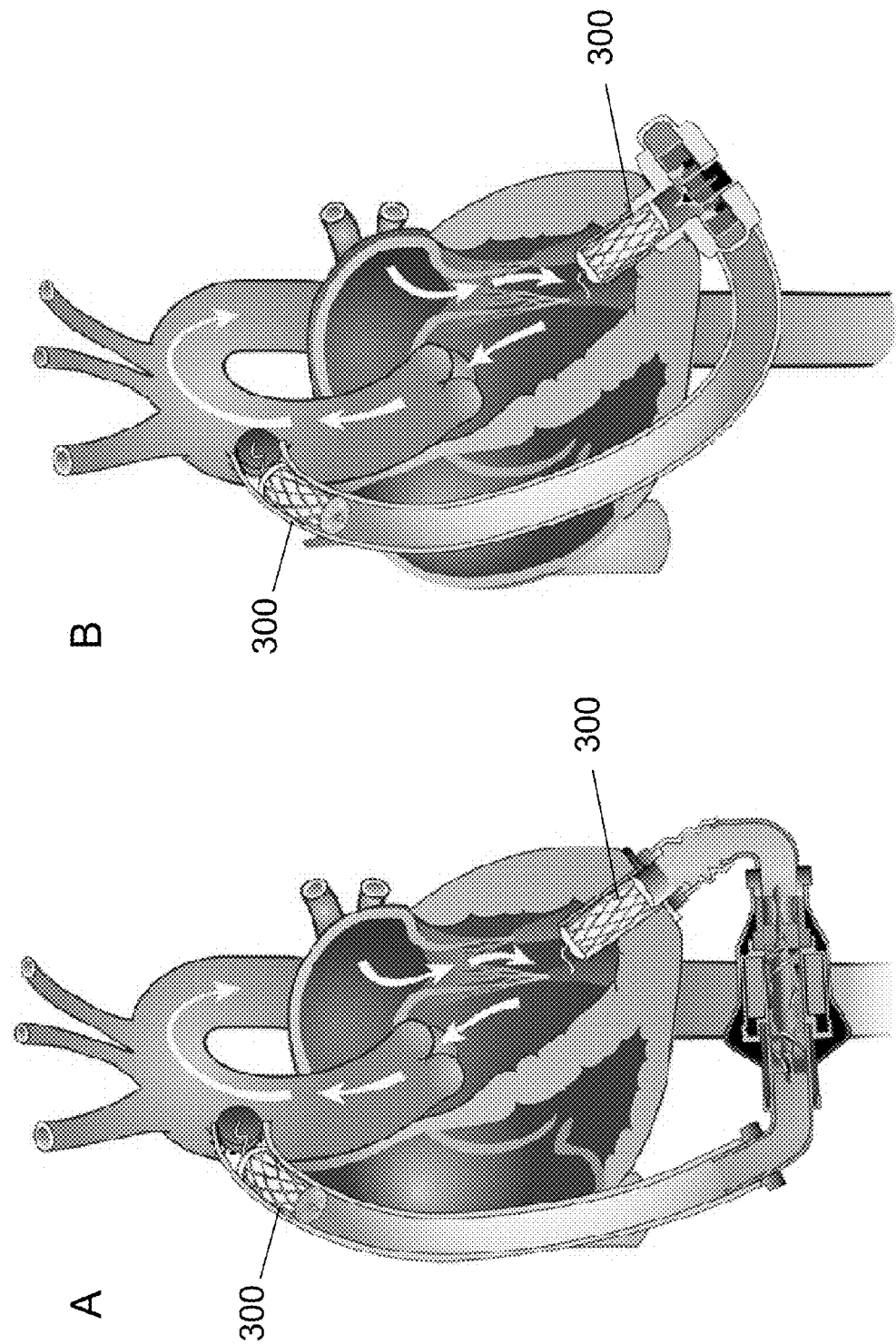
FIG. 11, comprising

As depicted in FIG. 11, in certain embodiments, the method comprises insertion of closure devices 300 at the inflow port and outflow port of the pump to block flow into and out of the pump for mid-term or permanent exclusion of the heart pump. Such closure devices 300 may be used when it is determined that native heart function is adequate to support sufficient blood supply to the entire body, and that the use of the heart pump is no longer necessary. Closure devices 300 can be guided to their appropriate location via a catheter, and can be left in the body for an extended period of time. In one embodiment, closure devices 300 are deformable, such that they are easily placed at the necessary site and effectively occlude blood flow. If it is later determined that native heart function has regressed to the point where the use of the pump would become beneficial or necessary, closure devices 300 can be removed.

Figure 15:
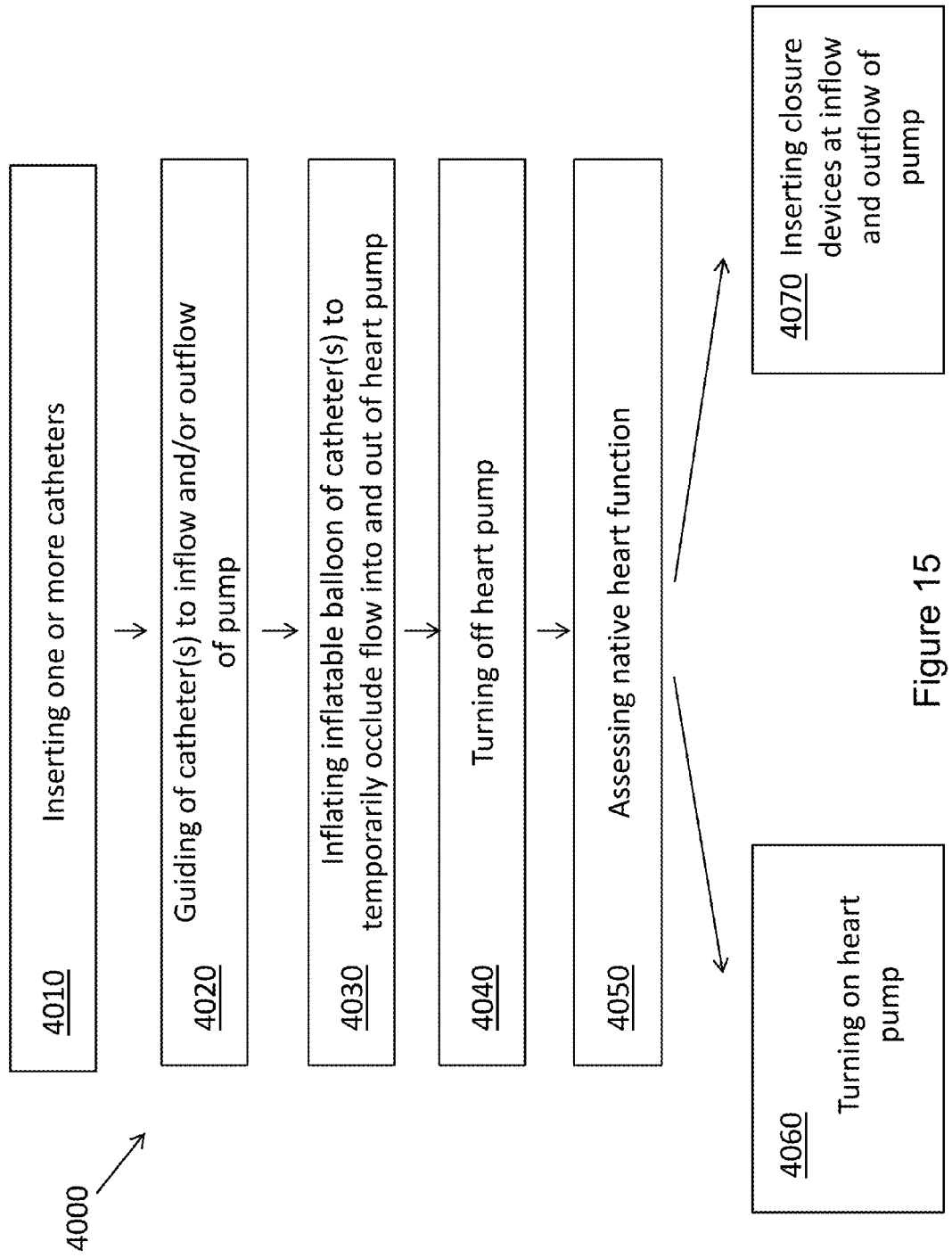
FIG. 15 depicts a flow chart illustrating an exemplary method of assessing native heart function in a subject having an implanted heart pump, and if native heart function is deemed adequate, insertion of closure devices to isolate the implanted pump from circulation.

FIG. 15 depicts a flow chart illustrating an exemplary method 4000 of assessing native heart function in a subject having an implanted heart pump. Method 4000 comprises inserting one or more catheters into the patient 4010, and guiding of the one or more catheters to the inflow and/or outflow of the heart pump 4020. In certain embodiments, the catheter comprises an inflatable balloon on the outer surface of the catheter. Inflating the balloon 4030 then occludes the inflow port or outflow port, preventing blood from entering or exiting. In one embodiment, method 4000 comprises turning off of the pump 4040. The turning off of pump 4040 may be done before or after guiding of the catheters 4020 and/or inflation of the balloon 4030. In one embodiment, method 4000 comprises assessing native heart function 4050, using standard methods known in the art. In certain embodiments, if native heart function is determined to be deficient, the implanted pump is turned back on 4060. If native heart function is determined to be adequate, closure devices are implanted into the inflow and outflow of the implanted heart pump 4070. In certain instances, the same implanted heart pump can be re-used if after some time the native heart function deteriorates and needs support. For example, the closure devices may be removed, the pump cleaned of any debris and washed, as described herein, and be re-used again in situ.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method for in situ inspection of an implanted heart pump comprising at least one inflow port, at least one outflow port and an interior chamber therebetween, the interior chamber including at least one mechanical component of the heart pump, the method comprising:
    guiding a catheter into the inflow port or outflow port of a heart pump implanted in a subject; and
    advancing a device component through an inner lumen of the catheter and into the interior chamber.

2. The method of claim 1, wherein the method comprises delivering a scope through an inner lumen of the catheter into an interior chamber of the heart pump to allow for visual inspection of the interior of the heart pump.

3. The method of claim 1, wherein the method comprises inflating a balloon positioned at the distal end of the catheter, thereby occluding blood flow.

4. A method for reducing the presence of blood clots within an implanted heart pump comprising at least one inflow port, at least one outflow port and an interior chamber therebetween, the interior chamber including at least one mechanical component of the heart pump, the method comprising:
    guiding a first catheter to the inflow port of a heart pump implanted in a subject;
    guiding a fluid delivery device through an inner lumen of the first catheter into the interior chamber of the heart pump; and
    administering a fluid to the interior of the heart pump, wherein the fluid reduces the presence of blood clots within the heart pump.

5. The method of claim 4, wherein the fluid delivery device is guided to the heart pump via the working channel of a scope, wherein the scope is guided to the heart pump via the inner lumen of the first catheter.

6. The method of claim 4, wherein the fluid comprises an anticoagulant selected from the group consisting of heparin, tissue plasminogen activator (tPa), streptokinase, collagenase, proteases, proteoltyic agents, superhydrophobic agents, and analogs thereof.

7. A method for in situ inspection of an implanted heart pump and excluding the heart pump from the blood flow circuit of a subject having the implanted heart pump, the heart pump comprising at least one inflow port, at least one outflow port and an interior chamber therebetween, the interior chamber including at least one mechanical component of the heart pump, the method comprising:
    guiding a first catheter to the inflow port of the heart pump;
    guiding a second catheter to the outflow port of the heart pump;
    occluding flow into the heart pump by positioning a first occlusion structure at the inflow port;
    occluding flow out of the heart pump by positioning a second occlusion structure at the outflow port; and
    advancing a device component through an inner lumen at least one of the first and second occlusion structure and into the interior chamber.

8. The method of claim 7, wherein the first and second occlusion structures each comprise an inflated balloon.

9. The method of claim 7, further comprising assessing the cardiac function of native heart tissue while the heart pump is excluded from the blood flow circuit.

10. The method of claim 7, wherein the first and second occlusion structures each comprise a closure device guided to the inflow port and outflow port via the first and second catheter.

11. The method of claim 10, wherein the closure device is manufactured from a material selected from the group consisting of titanium, stainless steel, nitinol, polyethylene terephthalate, polyether ether ketone, polyurethane, and graphene.

* * * * *